United States Patent
Nakamura et al.

(10) Patent No.: US 10,495,575 B2
(45) Date of Patent: *Dec. 3, 2019

(54) SURFACE PLASMON ENHANCED FLUORESCENCE MEASUREMENT DEVICE AND SURFACE PLASMON ENHANCED FLUORESCENCE MEASUREMENT METHOD

(71) Applicant: Konica Minolta, Inc., Tokyo (JP)

(72) Inventors: Yukito Nakamura, Saitama (JP); Takatoshi Kaya, Tokyo (JP); Kosuke Nagae, Tokyo (JP); Akitoshi Nozaki, Tokyo (JP); Fumio Nagai, Tokyo (JP); Ryouta Ishikawa, Tokyo (JP); Akiyuki Namatame, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 401 days.

This patent is subject to a terminal disclaimer.

(21) Appl. No.: 15/301,538

(22) PCT Filed: Apr. 8, 2014

(86) PCT No.: PCT/JP2014/002009
§ 371 (c)(1),
(2) Date: Oct. 3, 2016

(87) PCT Pub. No.: WO2015/155799
PCT Pub. Date: Oct. 15, 2015

(65) Prior Publication Data
US 2017/0030833 A1    Feb. 2, 2017

(51) Int. Cl.
*G01N 33/553*    (2006.01)
*G01N 21/64*    (2006.01)
*G01N 33/543*    (2006.01)

(52) U.S. Cl.
CPC ....... *G01N 21/648* (2013.01); *G01N 21/6428* (2013.01); *G01N 21/6445* (2013.01);
(Continued)

(58) Field of Classification Search
None
See application file for complete search history.

(56) References Cited

U.S. PATENT DOCUMENTS

| | | | |
|---|---|---|---|
| 6,274,872 B1 | 8/2001 | Katerkamp | |
| 2004/0150880 A1* | 8/2004 | Nakata | G02B 21/0068 359/386 |

(Continued)

FOREIGN PATENT DOCUMENTS

| | | |
|---|---|---|
| JP | 2000515966 A | 11/2000 |
| JP | 2010038624 A | 2/2010 |

(Continued)

OTHER PUBLICATIONS

K. Tawa, et al; Optical microscopic observation of fluorescence enhanced by grating-coupled surface . . . ; Optics Express; vol. 16; No. 13; Jun. 2008; pp. 9781-9790.

(Continued)

*Primary Examiner* — Christopher L Chin
(74) *Attorney, Agent, or Firm* — Lucas & Mercanti, LLP

(57) ABSTRACT

The present invention pertains to a surface plasmon enhanced fluorescence analysis device and a surface plasmon enhanced fluorescence measurement method which use GC-SPFS and make it possible to detect a substance to be detected with high sensitivity. This surface plasmon enhanced fluorescence measurement device has: a light source for irradiating the diffraction grating of a chip with excited light; a polarizer for removing linearly polarized light from fluorescent light emitted from a fluorescent substance on the diffraction grating; and a photodetector for
(Continued)

detecting the linearly polarized light removed by the polarizer.

5 Claims, 11 Drawing Sheets

(52) U.S. Cl.
CPC .......... *G01N 33/54373* (2013.01); *G01N 2021/6439* (2013.01); *G01N 2021/6463* (2013.01); *G01N 2201/0612* (2013.01); *G01N 2201/0683* (2013.01)

(56) References Cited

U.S. PATENT DOCUMENTS

| | | |
|---|---|---|
| 2005/0186565 A1 | 8/2005 | Malak |
| 2006/0193550 A1 | 8/2006 | Wawro et al. |
| 2015/0060697 A1* | 3/2015 | Umetsu ............... G01N 21/648 250/458.1 |

FOREIGN PATENT DOCUMENTS

| | | |
|---|---|---|
| JP | 2011158369 A | 8/2011 |
| JP | 2013-24607 A | 2/2013 |

OTHER PUBLICATIONS

International Search Report dated Jul. 15, 2014 for PCT/JP2014/002009 and English translation.
English translation of IPRP dated Jul. 15, 2014 for corresponding International Application; International Application No. PCT/JP2014/002009; Applicant: Konica Minolta,Inc.; Total of 7 pages.
Japanese Office Action and english translation, 2016-512486, dated Oct. 10, 2017.
Extended European Search Report dated Nov. 7, 2017 from the corresponding European Application No. 14889152.6.
Martin Bauch et al: "Plasmon-Enhanced Flurorescence Biosensors: a Review", Plasmonics, vol. 9, No. 4, Dec. 28, 2013, pp. 781-799, XP055151180.
Notice of Reasons for Rejection dated May 29, 2018 from corresponding Japanese Patent Application No. JP 2016-512486 and English translation.

* cited by examiner

SURFACE PLASMON ENHANCED FLUORESCENCE MEASUREMENT DEVICE AND SURFACE PLASMON ENHANCED FLUORESCENCE MEASUREMENT METHOD

CROSS REFERENCE TO RELATED APPLICATION

This Application is a 371 of PCT/JP2014/002009 filed on Apr. 8, 2014, application which is incorporated herein by reference.

TECHNICAL FIELD

The present invention relates to a surface plasmon enhanced fluorescence measurement device and a surface plasmon enhanced fluorescence measurement method for detecting the presence of or the amount of a detection object substance contained in a sample by utilizing surface plasmon resonance.

BACKGROUND ART

Highly sensitive and quantitative detection of a minute amount of a detection object substance such as protein and DNA in laboratory tests makes it possible to perform treatment by quickly determining the patient's condition. There is therefore a need for a method for quantitatively measuring a minute amount of detection object substance with high sensitivity.

Surface plasmon-field enhanced fluorescence spectroscopy (hereinafter abbreviated as "SPFS") is known as a method for detecting the detection object substance with high sensitivity. The SPFS utilizes a phenomenon in which surface plasmon resonance (hereinafter abbreviated as "SPR") is caused when a metal film irradiated with light under a certain condition. A capturing body (for example, primary antibody) which can be specifically coupled with a detection object substance is immobilized on a metal film, and thus a reaction site for specifically capturing the detection object substance is formed. When a sample containing the detection object substance is provided to the reaction site, the detection object substance is coupled with the reaction site. Next, when anther capturing body (for example secondary antibody) labeled with fluorescence material is provided to the reaction site, the detection object substance coupled with the reaction site is labeled with the fluorescence material. When the metal film is irradiated with excitation light in that state, the fluorescence material which labels the detection object substance is excited by the electric field enhanced by SPR, thus emitting fluorescence. Accordingly, the presence or the amount of the detection object substance can be measured by detecting the fluorescence. In SPFS, a fluorescence material is excited by the electric field enhanced by SPR, and therefore the detection object substance can be detected with high sensitivity.

SPFS is roughly categorized by the way of coupling excitation light and surface plasmon, into prism coupling (PC)-SPFS and grid coupling (GC)-SPFS. In PC-SPFS, a prism in which a metal film is formed on one surface is used. In this method, excitation light is totally reflected at the interface between the prism and the metal film to couple excitation light and surface plasmon. PC-SPFS is the mainstream method in recent years; however, PC-SPFS is disadvantageous in terms of downsizing of the measurement device since a prism is used and the incident angle of excitation light to the metal film is large in PC-SPFS.

In contrast, in GC-SPFS, excitation light and surface plasmon are coupled together by utilizing diffraction grating (see PTL 1 and non-PTL 1). GC-SPFS can downsize the measurement device in comparison with PC-SPFS since a prism is not used and the incident angle of excitation light to the diffraction grating is small in GC-SPFS.

CITATION LIST

Patent Literature

PTL 1
Japanese Patent Application Laid-Open No. 2011-158369

Non-Patent Literature

NPL 1
Keiko Tawa, Hironobu Hori, Kenji Kintaka, Kazuyuki Kiyosue, Yoshiro Tatsu, and Junji Nishii, "Optical microscopic observation of fluorescence enhanced by grating-coupled surface plasmon resonance", Optics Express, Vol. 16, pp. 9781-9790.

SUMMARY OF INVENTION

Technical Problem

As described above, GC-SPFS is advantageous in downsizing of the measurement device in comparison with PC-SPFS; however, research on GC-SPFS has not been developed in comparison with PC-SPFS. In view of this, measurement devices and measurement methods utilizing GC-SPFS have a room for improvement in detection sensitivity.

An object of the present invention is to provide a measurement device and a measurement method utilizing GC-SPFS which can detect the detection object substance with higher sensitivity.

Solution to Problem

To solve the above-mentioned problems, in a surface plasmon enhanced fluorescence measurement device according to embodiments of the present invention to which a chip is mounted, the chip includes a metal film on which a diffraction grating is formed, a capturing body immobilized on the diffraction grating, and a detection object substance coupled with the capturing body and labeled with a fluorescence material, the surface plasmon enhanced fluorescence measurement device being configured to detect presence or an amount of the detection object substance by irradiating the diffraction grating with excitation light, the surface plasmon enhanced fluorescence measurement device including: a light source configured to irradiate the diffraction grating with the excitation light to excite the fluorescence material with an enhanced electric field such that the fluorescence material emits fluorescence; a polarizer configured to extract linear polarization light from the fluorescence emitted from the fluorescence material; and a light detection section configured to detect the linear polarization light extracted by the polarizer.

To solve the above-mentioned problems, a surface plasmon enhanced fluorescence measurement method according to embodiments of the present invention is a method for detecting presence or an amount of a detection object substance by detecting fluorescence emitted from a fluorescence material excited with an electric field based on surface plasmon resonance, the fluorescence material labeling the detection object substance, the surface plasmon enhanced fluorescence measurement method including: preparing a chip including a metal film on which a diffraction grating is formed, a capturing body immobilized on the diffraction grating, and a detection object substance coupled with the capturing body and labeled with the fluorescence material; irradiating the diffraction grating with excitation light such that surface plasmon resonance is generated at the diffraction grating; extracting linear polarization light from fluorescence emitted from the fluorescence material; and detecting the linear polarization light.

Advantageous Effects of Invention

According to the present invention, in a measurement device and a measurement method utilizing GC-SPFS, the detection object substance can be detected with higher sensitivity. In addition, according to the present invention, the detection object substance can be detected in real time.

DESCRIPTION OF EMBODIMENTS

Embodiments of the present invention are described in detail below with reference to the accompanying drawings.

Embodiment 1

Figure 1:
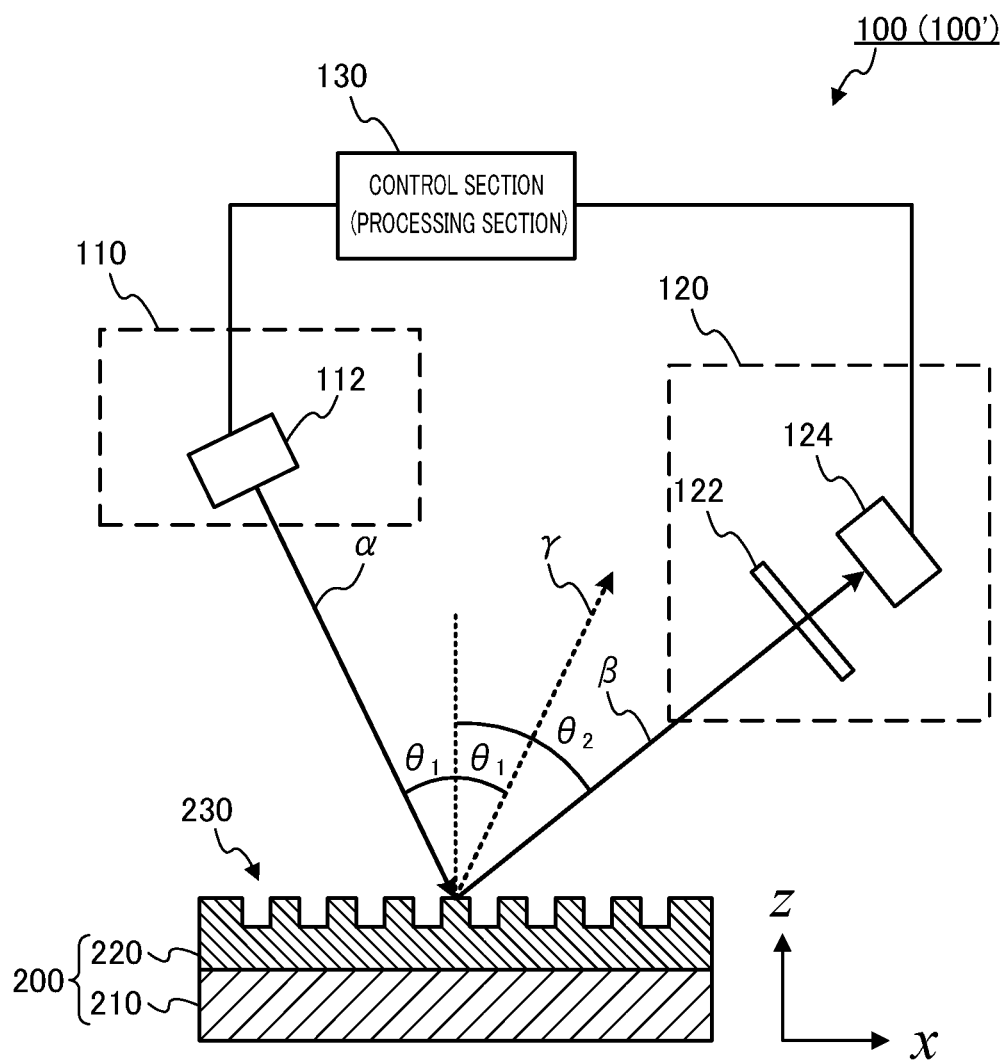
FIG. 1 is a schematic view illustrating a configuration of surface plasmon enhanced fluorescence measurement devices (hereinafter referred to as "SPFS devices") according to Embodiments 1 and 2.

FIG. 1 is a schematic view illustrating a configuration of surface plasmon enhanced fluorescence measurement device (SPFS device) 100 according to Embodiment 1 of the present invention.

As illustrated in FIG. 1, SPFS device 100 includes excitation light irradiation unit 110, fluorescence detection unit 120 and control section 130. SPFS device 100 is used with chip 200 attached to a chip holder (not illustrated). For such a configuration, chip 200 is described first, and then SPFS device 100 is described.

Chip 200 includes substrate 210, and metal film 220 formed on substrate 210. In metal film 220, diffraction grating 230 is formed. A capturing body (for example, a primary antibody) is immobilized on diffraction grating 230, and the surface of diffraction grating 230 functions also as a reaction site for coupling between the capturing body and the detection object substance. It is to be noted that in FIG. 1, the capturing body and the detection object substance are omitted.

Substrate 210 is a supporting member of metal film 220. The material of substrate 210 is not limited as long as substrate 210 has a mechanical strength enough to support metal film 220. Examples of the material of substrate 210 include inorganic materials such as glass, quartz and silicon, and resins such as polymethylmethacrylate, polycarbonate, polystyrene, and polyolefin.

Metal film 220 is disposed on substrate 210. As described above, diffraction grating 230 is formed in metal film 220. When metal film 220 is irradiated with light, surface plasmon generated in metal film 220 and the evanescent wave generated by diffraction grating 230 are coupled together, and surface plasmon resonance is generated. The material of metal film 220 is not limited as long as the material is a metal which generates surface plasmon. Examples of the material of metal film 220 include gold, silver, copper, aluminum, and alloys thereof. The formation method of metal film 220 is not limited. The examples of the formation method of metal film 220 include sputtering, depositing, and plating. The thickness of metal film 220 is not limited. Metal film 220 has a thickness of 30 to 500 nm, preferably, 100 to 300 nm, for example.

Figure 2A:
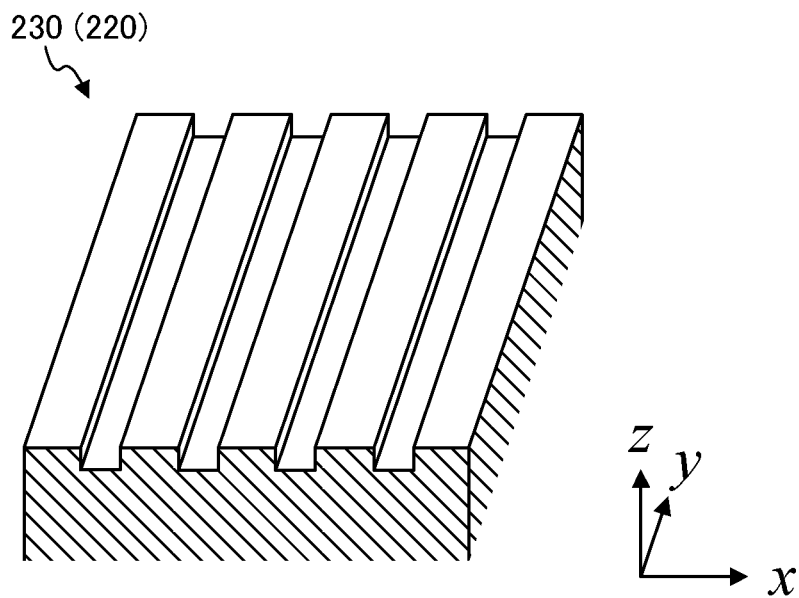
FIGS. 2A and 2B are perspective views of a diffraction grating.
Figure 2B:
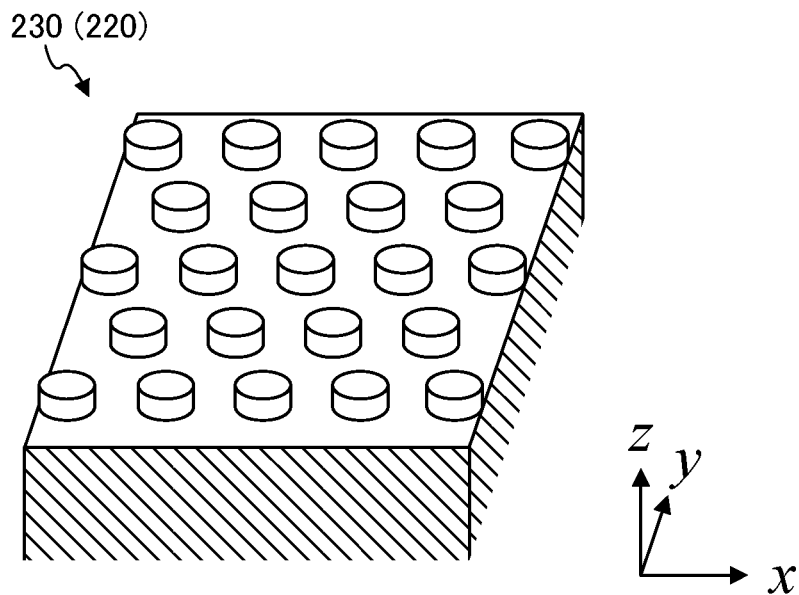

When metal film 220 is irradiated with light, diffraction grating 230 generates evanescent wave. The shape of diffraction grating 230 is not limited as long as evanescent wave can be generated. For example, diffraction grating 230 may be a one-dimensional diffraction grating as illustrated in FIG. 2A, or may be a two-dimensional diffraction grating as illustrated in FIG. 2B. In the one-dimensional diffraction grating illustrated in FIG. 2A, a plurality of projected lines parallel to each other are formed on the surface of metal film 220 at predetermined intervals. In the two-dimensional diffraction grating illustrated in FIG. 2B, protrusions having a predetermined shape are cyclically disposed on the surface of metal film 220. Examples of the way of arranging the protrusions include square grating, triangle (hexagonal) grating and the like. Examples of the cross-sectional shape of diffraction grating 230 include rectangular-wave shapes, sine-wave shapes, saw-tooth shapes and the like. In the examples illustrated in FIGS. 2A and 2B, the optical axis of excitation light α described later is parallel to the xz-plane.

The formation method of diffraction grating 230 is not limited. For example, irregularity may be provided on metal film 220 after metal film 220 is formed on plate-shaped substrate 210. In addition, metal film 220 may be formed on substrate 210 on which irregularity has been provided in advance. Metal film 220 having diffraction grating 230 may be formed with any method.

A capturing body for capturing the detection object substance is immobilized on diffraction grating 230 (reaction site). The capturing body is specifically coupled to the detection object substance. In the present embodiment, the capturing body is substantially uniformly immobilized on the surface of diffraction grating 230. The kind of the capturing body is not limited as long as the detection object substance can be captured. For example, the capturing body is an antibody (primary antibody) specific to the detection object substance or its fragments, or, an enzyme which can be specifically coupled to the detection object substance.

The way of immobilizing the capturing body is not limited. For example, it suffices to form a polymer film or a self-organizing monomolecular film (hereinafter referred to as "SAM") coupled with a capturing body on diffraction grating 230. Examples of the SAM include a film formed of substituted aliphatic thiol such as $HOOC-(CH_2)_{11}-SH$. Examples of the material of the polymer film include polyethylene glycol and MPC polymer. In addition, it is also possible to immobilize a polymer having a reactive group which can be coupled with the capturing body (or a functional group which can be converted to a reactive group) on diffraction grating 230, and couple a capturing body to the polymer.

As illustrated in FIG. 1, excitation light α is applied to metal film 220 (diffraction grating 230) at a predetermined incident angle $\theta_1$. In the region irradiated with the light, the surface plasmon generated at metal film 220 and the evanescent wave generated by diffraction grating 230 are coupled together, and SPR occurs. In the case where a fluorescence material is present in the region irradiated with the light, the fluorescence material is excited by the enhanced electric field formed by SPR, and fluorescence β is emitted. In GC-SPFS, fluorescence β is emitted with directivity in a specific direction unlike the case of PC-SPFS. For example, emission angle $\theta_2$ of fluorescence β is approximated as $2\theta_1$. It is to be noted that almost no reflection light γ of excitation light α is generated.

Figure 3A:
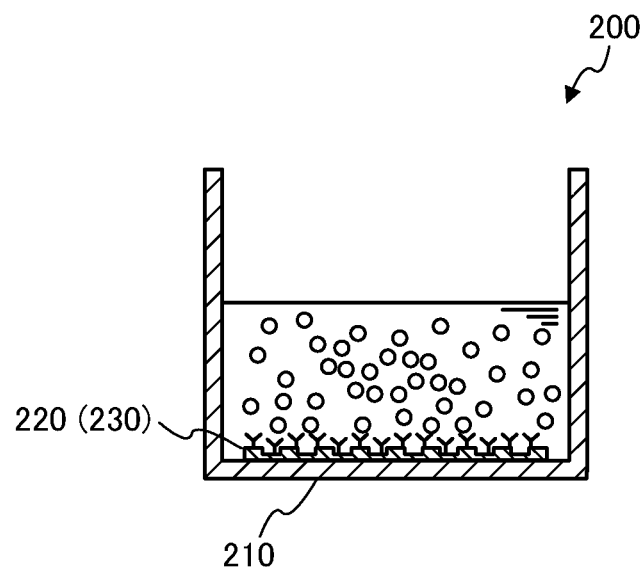
FIG. 3A schematically illustrates a first mode of a chip according to Embodiments 1 and 2, and FIG. 3B schematically illustrates a second mode of the chip according to Embodiments 1 and 2.
Figure 3B:
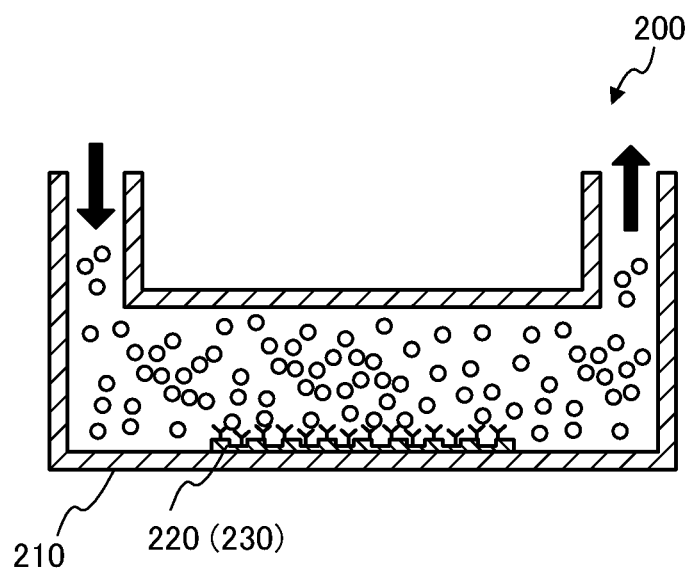

When in use, diffraction grating 230 makes contact with liquid such as buffer solution for operations such as reaction and washing. Accordingly, normally, diffraction grating 230 is disposed in a space which can contain liquid. For example, diffraction grating 230 may be disposed on the internal surface (for example, the bottom surface) of a well which houses liquid as illustrated in FIG. 3A, or may be disposed on the internal surface (for example, the bottom surface) of a channel (flow cell) to which liquid can be successively supplied as illustrated in FIG. 3B. For example, chip 200 illustrated in FIG. 3A is also suitable for material movement analysis (real time measurement; see Embodiment 2) in a space between the bulk and the surface of metal film 220, measurement of an enhanced electric field space scale (z-axis direction) and the like in addition to common measurement of a detection object substance (non-real time measurement). For example, chip 200 illustrated in FIG. 3B is also suitable for reaction constant analysis (real time measurement; see Embodiment 2) of molecules (detection object substance) other than molecules (capturing body) immobilized on the surface of metal film 220, and the like in addition to common measurement of a detection object substance (non-real time measurement).

Next, components of SPFS device 100 are described.

Excitation light irradiation unit 110 irradiates metal film 220 (diffraction grating 230) of chip 200 with excitation light α having a constant wavelength and a constant light quantity. At this time, excitation light irradiation unit 110 irradiates metal film 220 (diffraction grating 230) with p-polarization light with respect to the surface of metal film 220 such that diffraction light which can be coupled with the surface plasmon in metal film 220 is generated at diffraction grating 230. The optical axis of excitation light α extends along the arrangement direction of diffraction grating 230 having a cyclic structure (the x-axis direction in FIGS. 2A and 2B). Accordingly, when the y-axis is defined as the axis perpendicular to the x-axis and parallel to the surface of metal film 220, and the z-axis is defined as the axis perpendicular to the x-axis and perpendicular to the surface of metal film 220, the optical axis of excitation light α is parallel to the xz-plane (see FIG. 1). Since excitation light α is p-polarization light with respect to the surface of metal film 220, the direction of the electric field oscillation of excitation light α is parallel to the xz-plane which includes the optical axis of excitation light α and the normal to the surface of metal film 220.

Excitation light irradiation unit 110 includes at least light source 112. Excitation light irradiation unit 110 may further include a collimator lens, an excitation light filter and the like.

Light source 112 emits excitation light α toward diffraction grating 230 of chip 200. In the present embodiment, light source 112 is a laser diode. It is to be noted that the kind of light source 112 is not limited, and light source 112 may not be a laser diode. Examples of light source 112 include light-emitting diodes, mercury lamps, and other laser light sources.

The collimator lens (omitted in the drawing) is disposed between light source 112 and chip 200, and configured to collimate excitation light α emitted from light source 112. The outline shape of excitation light α emitted from laser diode (light source 112) is flat even after collimation. In view of this, the laser diode is held at a predetermined orientation such that the irradiation spot on the surface of metal film 220 has a substantially circular shape. Preferably, the irradiation spot has a size of about 1 mmφ, for example.

The excitation light filter (omitted in the drawing) is disposed between light source 112 and chip 200, and configured to regulate excitation light α emitted from light source 112. For example, the excitation light filter includes a band pass filter and a linear polarization filter. Since excitation light α from the laser diode (light source 112) has a slight wavelength distribution width, the band pass filter converts the excitation light α from laser diode into narrowband light composed only of the central wavelength. In addition, since excitation light α from the laser diode (light source 112) is not completely-linear polarization, the linear polarization filter converts the excitation light α from the laser diode into complete linear polarization light. The excitation light filter may include a half-wave plate for regulating the polarization direction of excitation light α such that p-polarization light is incident on metal film 220.

Preferably, incident angle $\theta_1$ of excitation light α to metal film 220 (see FIG. 1) is an angle at which the intensity of the enhanced electric field formed by SPR is maximized, and as a result the intensity of fluorescence β from the fluorescence material is maximized. Incident angle $\theta_1$ of excitation light α is appropriately selected in accordance with the pitch of diffraction grating 230, the wavelength of excitation light α, the metal of metal film 220 and the like. Preferably, the pitch of the diffraction grating is about 400 nm for example. Optimum incident angle $\theta_1$ of excitation light α differs depending on the conditions, and therefore SPFS device 100 preferably includes a first angle adjusting section (omitted in the drawing) configured to adjust incident angle $\theta_1$ by relatively rotating the optical axis of excitation light α and chip 200. For example, it suffices that the first angle adjusting section rotates excitation light irradiation unit 110 or chip 200 around the intersection of the optical axis of excitation light α and metal film 220 as the center.

Fluorescence detection unit 120 is disposed such that a straight line which passes through the intersection of the optical axis of excitation light α and metal film 220 and is perpendicular to the surface of metal film 220 is interposed between fluorescence detection unit 120 and excitation light irradiation unit 110. Fluorescence detection unit 120 detects fluorescence β emitted from the fluorescence material on diffraction grating 230 (reaction site).

Fluorescence detection unit 120 includes at least polarizer 122 and light detection section 124. Fluorescence detection unit 120 may further include a condenser lens group, an opening diaphragm, a fluorescence filter and the like.

Polarizer 122 is disposed between chip 200 and light detection section 124, and configured to extract linear polarization light from fluorescence β emitted from the fluorescence material. In the present embodiment, polarizer 122 is a polarization plate. Polarizer 122 is held such that polarizer 122 can rotate in a plane perpendicular to the travelling direction of fluorescence β travelling from metal film 220 toward light detection section 124.

Polarizer 122 simultaneously or separately extracts, from fluorescence β, first light in which the angle of the direction of the electric field oscillation with respect to the plane including the normal to the surface of metal film 220 and the optical axis of excitation light α (the xz-plane) is 0±30°, and second light in which the angle of the direction of the electric field oscillation with respect to the plane (the xz-plane) is 90±30°. Preferably, polarizer 122 simultaneously or separately extracts, from fluorescence β, p-polarization light in which the angle of the direction of the electric field oscillation with respect to the plane (the xz-plane) is 0° as the first light, and s-polarization light in which the angle of the direction of the electric field oscillation with respect to the plane (the xz-plane) is 90° as the second light. In the present embodiment, polarizer (polarization plate) 122 is rotated to thereby separately extract the first light (for example, p-polarization light) and the second light (for example, s-polarization light). As described later, the first light is light containing a signal component and a noise component of the detection object, and the second light is light mainly composed of a noise component.

The kind of polarizer 122 is not limited as long as linear polarization light in a predetermined polarization direction can be extracted, and polarizer 122 may not be a polarization plate. Examples of polarizer 122 include a polarization prism, a liquid crystal filter, and other polarization filters.

Light detection section 124 detects the linear polarization light extracted by polarizer 122 and detects the fluorescence image on metal film 220. In the case where the first light and the second light are simultaneously or separately extracted by polarizer 122 from fluorescence β, light detection section 124 detects each of the first light and the second light. For example, light detection section 124 is a photomultiplier tube having a high sensitivity and a high S/N ratio. Light detection section 124 may also be an avalanche photodiode (APD), a photodiode (PD), a CCD image sensor or the like.

The condenser lens group (omitted in the drawing) is disposed between chip 200 and light detection section 124, and serves as a conjugate optical system which is not easily influenced by stray light. The condenser lens group brings the fluorescence image on metal film 220 into an image on the light reception surface of light detection section 124.

The fluorescence filter (omitted in the drawing) is disposed between chip 200 and light detection section 124. For example, the fluorescence filter includes a cut filter and a neutral density (ND) filter. The fluorescence filter extracts, from the light reaching light detection section 124, noise components (such as excitation light α and external light) other than fluorescence β, and adjusts the quantity of light reaching light detection section 124.

As described above, in GC-SPFS, fluorescence β is emitted from diffraction grating 230 (reaction site) with directivity in a specific direction. Accordingly, the angle of the optical axis of fluorescence detection unit 120 with respect to the normal to the surface of metal film 220 is preferably an angle at which the intensity of fluorescence β is maximized (fluorescence peak angle). Accordingly, SPFS device 100 preferably includes a second angle adjusting section (omitted in the drawing) configured to adjust the angle of the optical axis of fluorescence detection unit 120 by relatively rotating the optical axis of fluorescence detection unit 120 and chip 200. For example, it suffices that the second angle adjusting section rotates fluorescence detection unit 120 or chip 200 around the intersection of the optical axis of fluorescence detection unit 120 and metal film 220 as the center.

Control section 130 controls the operations of excitation light irradiation unit 110 (light source 112), fluorescence detection unit 120 (polarizer 122 and light detection section 124), excitation light irradiation unit 110 and the angle adjusting section (first angle adjusting section and second angle adjusting section) of fluorescence detection unit 120. In addition, control section 130 also functions as a processing section configured to process an output signal (detection result) from light detection section 124. For example, control section 130 is a computer configured to execute software.

Figure 4:
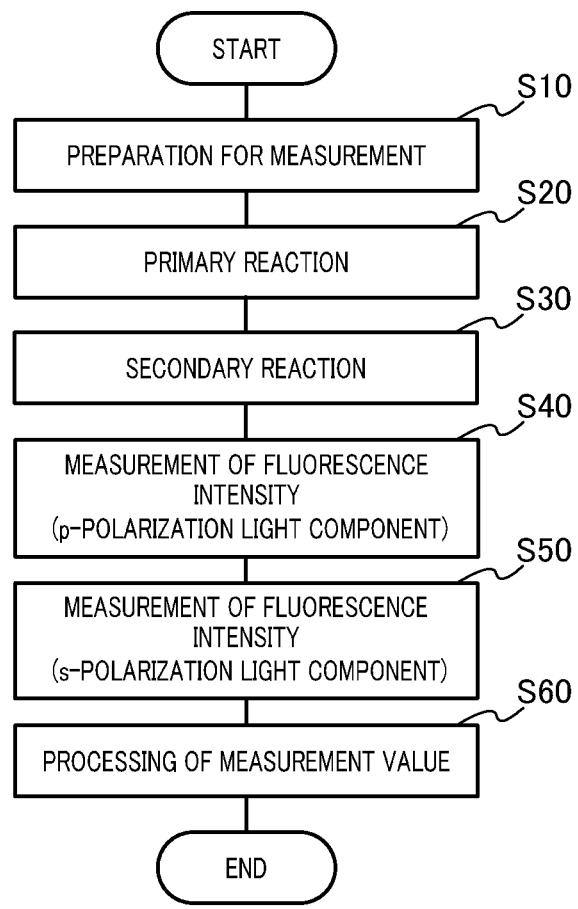
FIG. 4 is a flowchart of an operation of the SPFS device according to Embodiment 1.

Next, a detection operation of SPFS device 100 is described. FIG. 4 is a flowchart of example operation procedure of SPFS device 100. In this example, a primary antibody as a capturing body is immobilized on metal film 220. In addition, a secondary antibody labeled with a fluorescence material is used as the capturing body used for fluorescence labelling.

First, preparation for measurement is performed (step S10). Specifically, chip 200 is prepared, and installed at a predetermined position in SPFS device 100. In addition, in the case where a moisturizing agent is present on metal film 220 of chip 200, the surface of metal film 220 is washed to remove the moisturizing agent so that the primary antibody can appropriately capture the detection object substance.

Next, a reaction between the detection object substance in the sample and the primary antibody is caused (primary reaction, step S20). To be more specific, the sample is provided on metal film 220, and the sample and the primary antibody are brought into contact with each other. When the detection object substance is present in the sample, at least a part of the detection object substance is coupled to the primary antibody. Thereafter, the surface of metal film 220 is washed with buffer solution or the like to remove materials which have not been coupled to the primary antibody. The kind of the sample and the detection object substance is not limited. Examples of the sample include bodily fluids such as blood, serum, plasma, urine, nasal mucus, saliva, and semen, and their diluted solutions. Examples of the detection object substance include nucleic acid (such as DNA and RNA), protein (such as polypeptides and oligopeptides), amino acid, glucide, lipid and modifier molecules thereof.

Next, the detection object substance coupled with the primary antibody is labeled with the fluorescence material (secondary reaction, step S30). To be more specific, fluorescence labeling solution containing the secondary antibody labeled with the fluorescence material is provided on metal film 220, and the detection object substance coupled with the primary antibody and the fluorescence labeling solution are brought into contact with each other. The fluorescence labeling solution is buffer solution containing the secondary antibody labeled with the fluorescence material, for example. When the detection object substance is coupled with the primary antibody, at least a part of the detection object substance is labeled with the fluorescence material. As described later, in SPFS device 100 according to the present embodiment, the object substance can be detected without removing the free secondary antibody. However, after the labelling with the fluorescence material, it is preferable to wash the surface of metal film 220 with buffer solution or the like to remove the free secondary antibody and the like.

It is to be noted that the order of the primary reaction and the secondary reaction is not limited to the above-mentioned order. For example, it is also possible to, after the detection object substance is coupled with the secondary antibody, provide liquid containing the composite material thereof onto metal film 220. In addition, it is also possible to simultaneously provide the sample and the fluorescence labeling solution.

Figure 5A:
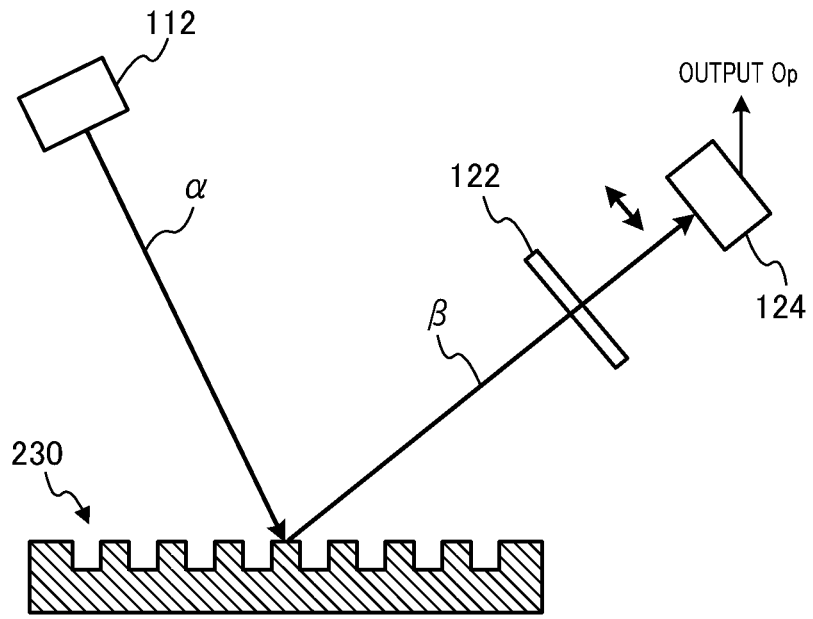
FIGS. 5A and 5B are schematic views illustrating procedure of measurement of the intensity of the fluorescence.

Next, metal film 220 is irradiated with excitation light α to measure the intensity of first light (for example, p-polarization light) contained in fluorescence β emitted from the fluorescence material (step S40). To be more specific, control section 130 controls light source 112 to emit excitation light α. At the same time, control section 130 controls light detection section 124 to detect the intensity of fluorescence β from metal film 220. At this time, as illustrated in FIG. 5A, control section 130 adjusts the rotation angle of polarizer 122 such that only first light (p-polarization light in the drawing) contained in fluorescence β is allowed to pass therethrough. Light detection section 124 outputs the measurement result (output Op) to control section (processing section) 130.

As shown in the reference experiment later, in GC-SPFS, the fluorescence β (signal component) emitted from the fluorescence material which labels the detection object substance is p-polarization light with respect to the surface of metal film 220, or light close to the p-polarization light in terms of the polarization angle. Accordingly, the signal component passes through polarizer 122 and reaches light detection section 124. On the other hand, the fluorescence β(noise component) emitted from the fluorescence material floating in liquid on metal film 220 is random polarization light. Accordingly, a part of the noise component (light having a polarization angle identical to that of the signal component) also passes through polarizer 122 and reaches light detection section 124. As a result, the measurement result (output Op) of this step contains the signal component and the noise component.

Figure 5B:
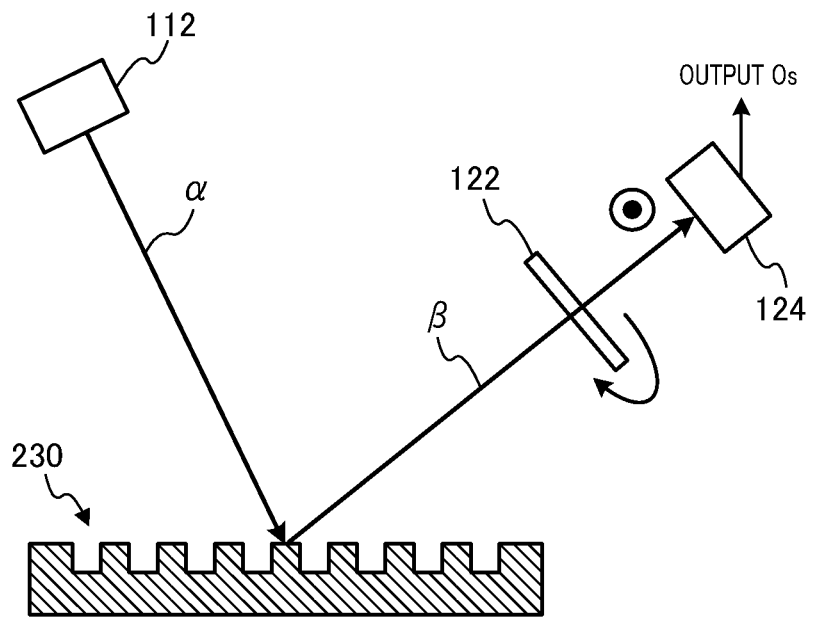

Next, metal film 220 is irradiated with excitation light α to measure the intensity of the second light (for example, s-polarization light) contained in fluorescence β emitted from the fluorescence material (step S50). To be more specific, control section 130 controls light source 112 to emit excitation light α. At the same time, control section 130 controls light detection section 124 to detect the intensity of fluorescence β from metal film 220. At this time, as illustrated in FIG. 5B, control section 130 adjusts the rotation angle of polarizer 122 such that only second light (s-polarization light in the drawing) contained in fluorescence β is allowed to pass therethrough. Light detection section 124 outputs the measurement result (output Os) to control section (processing section) 130.

As described in the previous step, the fluorescence β(noise component) emitted from the fluorescence material floating in liquid on metal film 220 is random polarization light. Accordingly, also in this step, a part of the noise component passes through polarizer 122 and reaches light detection section 124. As a result, the measurement result (output Os) of this step is mainly composed of the noise component.

It is to be noted that the order of the measurement of the first light (step S40) and the measurement of the second light (step S50) is not limited to the above-mentioned order. For example, the intensity of the first light may be measured after the intensity of the second light is measured.

Figure 6:
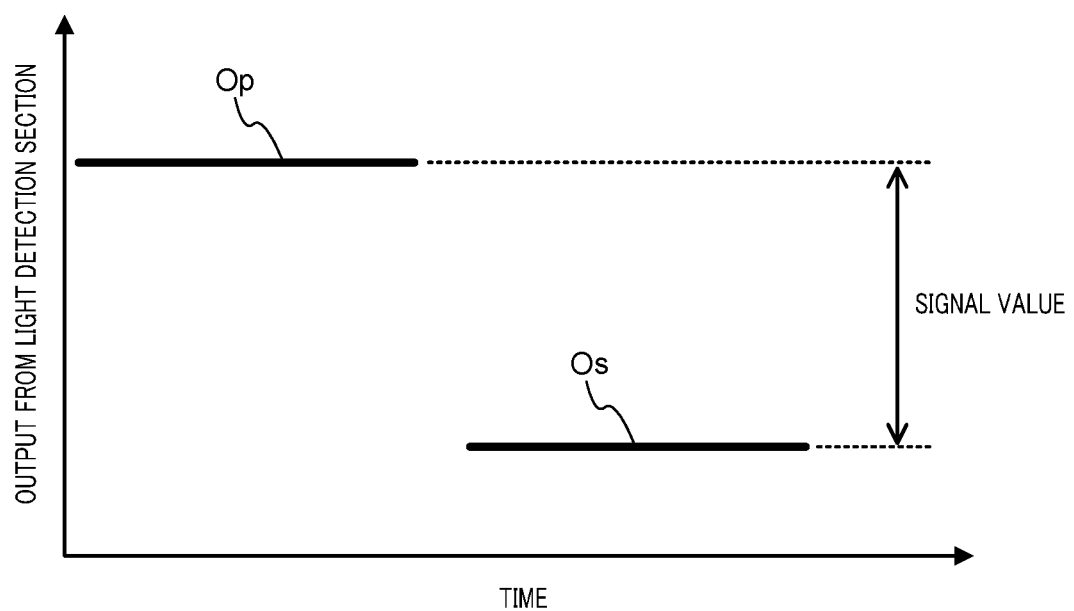
FIG. 6 is a graph for describing a difference value (signal value)

Finally, control section (processing section) 130 analyzes the output signal (output Op and Os) from light detection section 124 to analyze the presence of the detection object substance or the amount of the detection object substance (step S60). To be more specific, as illustrated in FIG. 6, control section (processing section) 130 calculates the difference value between output Op and output Os to obtain the signal value. As described above, output Op is mainly composed of the signal component and the noise component, and output Os is mainly composed of the noise component, and therefore, the signal value from which the noise component is removed can be obtained by calculating the difference value therebetween.

Through the above-mentioned procedure, the presence of the detection object substance or the amount of the detection object substance in the sample can be detected.

As described above, SPFS device 100 of the present embodiment can detect only the signal component by utilizing the difference between the signal component and the noise component in polarization characteristics, and therefore can detect the detection object substance with higher sensitivity in comparison with conventional SPFS devices.

In addition, SPFS device 100 of the present embodiment can remove the noise component contained in fluorescence β, and therefore the object substance can be detected without removing the free secondary antibody after the secondary reaction (step S30).

While chip 200 is irradiated with excitation light α from the metal film 220 side in the above-mentioned embodiment, chip 200 may be irradiated with excitation light α from the substrate 210 side.

Embodiment 2

SPFS device 100' according to Embodiment 2 has a configuration identical to that of SPFS device 100 according to Embodiment 1 except that real time measurement is performed. In view of this, description of the configuration of the SPFS device is omitted, and only the operation procedure is described below.

SPFS device 100' according to the present embodiment continuously irradiates diffraction grating 230 with excitation light α, and continuously extracts linear polarization light from fluorescence β emitted from the fluorescence material, and, continuously detects the linear polarization light. Here, the term "continue" includes not only successive operations, but also intermittent operations. Accordingly, "continuously emit excitation light" means that excitation light α is emitted for an appropriate period and with an appropriate frequency which allow for detection of the time variation of the detection object substance. "Linear polarization light is continuously extracted" means that linear polarization light is continuously extracted from fluorescence β for an appropriate period and with an appropriate frequency which allow for detection of the time variation of the detection object substance. "Linear polarization light is continuously detected" means that linear polarization light is detected from fluorescence β for an appropriate period and with an appropriate frequency which allow for detection of the time variation of the detection object substance.

For example, continuous irradiation with excitation light α may be successive irradiation with excitation light α, or intermittent irradiation with excitation light α. From the view point of preventing discoloration of the fluorescence material, it is preferable that the continuous irradiation with excitation light α be the intermittent irradiation of excitation light α. In this case, the interval of irradiation of excitation light α may be fixed or not fixed (any interval). In addition, the interval of irradiation of excitation light α may be automatically determined under a certain condition such as automatic calculation by a program, or empirically determined by a preliminary experiment or the like, or, arbitrarily determined by the user, for example.

The irradiation interval of the excitation light may be determined in accordance with the detection result of the intensity of the fluorescence. For example, the interval may be determined such that the irradiation interval of excitation light is reduced when the value of the detected intensity of the fluorescence is small, and the irradiation interval of excitation light is increased when the value of the detected intensity of the fluorescence is large. In addition, the interval may be determined such that the irradiation interval of excitation light is reduced when the time variation of the value of the detected intensity of the fluorescence is large, and the irradiation interval of excitation light is increased when the time variation of the value of the detected intensity of the fluorescence is small. The above-mentioned adjustment of the irradiation interval of excitation light can be achieved by properly setting a threshold according to the value of the detected intensity of the fluorescence, and by performing feedback control based on the value of the detected intensity of the fluorescence, for example. The above-mentioned adjustment of the irradiation interval of excitation light is preferable from the viewpoint of precisely observing the time variation of the detection object substance.

The same applies to the timing of continuous extraction of linear polarization light, and the timing of continuous detection of linear polarization light.

Figure 7:
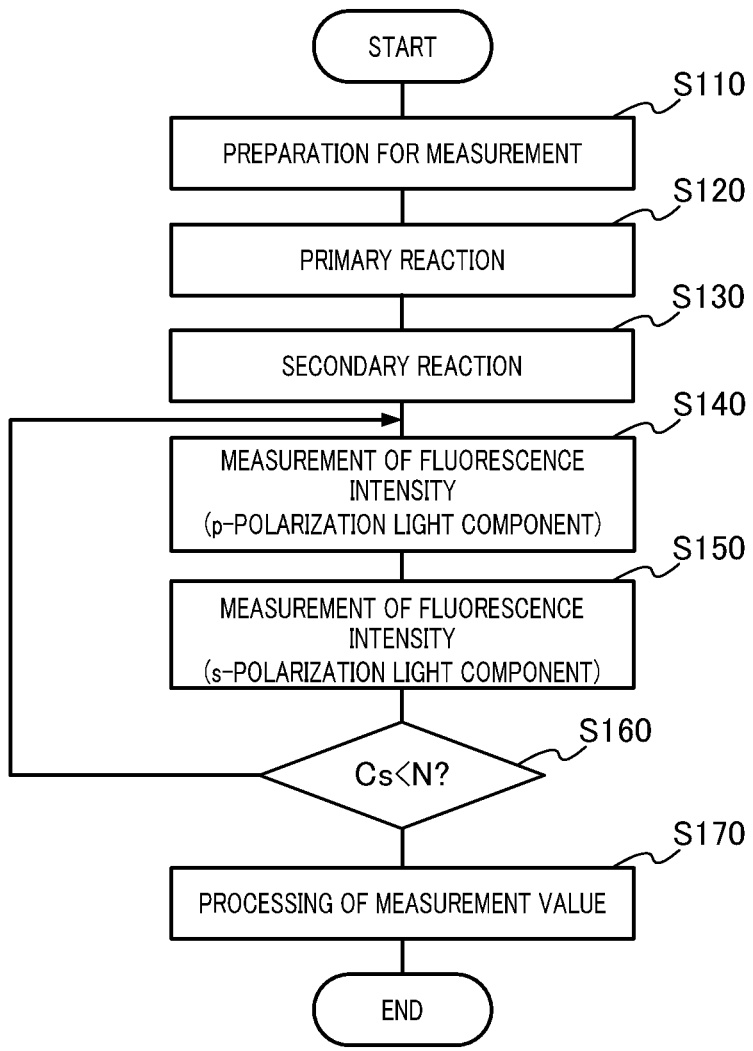
FIG. 7 is a flowchart of an operation of a SPFS device according to Embodiment 2.

FIG. 7 is a flowchart of an example operation procedure of SPFS device 100' according to Embodiment 2. In this example, a primary antibody as a capturing body is immobilized on metal film 220. In addition, a secondary antibody labeled with a fluorescence material is used as the capturing body used for fluorescence labelling.

First, preparation for measurement is performed (step S110). Specifically, chip 200 is prepared, and installed at a predetermined position in SPFS device 100'. As with Embodiment 1, the surface of metal film 220 is washed as necessary.

Next, a reaction between the detection object substance in the sample and the primary antibody is caused (primary reaction, step S120). To be more specific, the sample is provided on metal film 220, and the sample and the primary antibody are brought into contact with each other. When the detection object substance is present in the sample, at least a part of the detection object substance is coupled to the primary antibody. Thereafter, the surface of metal film 220 is washed with buffer solution or the like to remove materials which have not been coupled to the primary antibody.

Next, the detection object substance coupled with the primary antibody is labeled with the fluorescence material (secondary reaction, step S130). To be more specific, fluorescence labeling solution containing the secondary antibody labeled with the fluorescence material is provided on metal film 220, and the detection object substance coupled with the primary antibody and the fluorescence labeling solution are brought into contact with each other. The fluorescence labeling solution is buffer solution containing the secondary antibody labeled with the fluorescence material, for example. When the detection object substance is coupled with the primary antibody, at least a part of the detection object substance is labeled with the fluorescence material. As with Embodiment 1, SPFS device 100' according to the present embodiment can measure the detection object substance without removing the free secondary antibody.

It is to be noted that the order of the primary reaction and the secondary reaction is not limited to the above-mentioned order. For example, it is also possible to, after the detection object substance is coupled with the secondary antibody, provide liquid containing the composite material thereof onto metal film 220. In addition, it is also possible to simultaneously provide the sample and the fluorescence labeling solution.

Next, the intensity of first light (for example, p-polarization light) contained in fluorescence β emitted from the fluorescence material is measured while irradiating metal film 220 with excitation light α (step S140), and the intensity of the second light (for example, s-polarization light) contained in fluorescence β emitted from the fluorescence material is measured while irradiating metal film 220 with excitation light α (step S150). Then, measurement of the intensity of the first light and measurement of the intensity of the second light are repeated predetermined times (step S160). In this manner, measurement of the intensity of the first light and measurement of the intensity of the second light are alternately repeated multiple times, and both of the measurement value of the intensity of the first light and the measurement value of the intensity of the second light are continuously (intermittently) obtained.

To be more specific, at step S140, control section 130 controls light source 112 to emit excitation light α successively or intermittently at a predetermined interval (that is, "continuously"). The "predetermined interval" is the interval of changing (adjusting) the rotation angle of polarizer 122 described later. At the same time, control section 130 controls light detection section 124 to continuously detect the intensity of fluorescence β from metal film 220. The timing of the continuous detection of the intensity of fluorescence β may be synchronized with the temporal timing of irradiation of excitation light α, or may be different from the temporal timing of irradiation of excitation light α. At this time, control section 130 adjusts the rotation angle of polarizer 122 such that only first light (p-polarization light in the drawing) contained in fluorescence β is allowed to pass therethrough as illustrated in FIG. 5A. Light detection section 124 outputs the measurement result (output Op) to control section (processing section) 130.

As described in step S40 of Embodiment 1, fluorescence β(signal component) emitted from the fluorescence material which labels the detection object substance passes through polarizer 122 and reaches light detection section 124. On the other hand, part of the fluorescence β(noise component) emitted from the fluorescence material floating in liquid on metal film 220 (light having a polarization angle identical to that of the signal component) also passes through polarizer 122 and reaches light detection section 124. As a result, the measurement result (output Op) of this step contains the signal component and the noise component.

At step S150, control section 130 still controls light source 112 to continuously emit excitation light α. At the same time, control section 130 controls light detection section 124 to continuously detect the intensity of fluorescence β from metal film 220. At this time, as illustrated in FIG. 5B, control section 130 adjusts the rotation angle of polarizer 122 such that only second light (s-polarization light in the drawing) contained in fluorescence β is allowed to pass therethrough. Light detection section 124 outputs the measurement result (output Os) to control section (processing section) 130.

As described in step S50 of Embodiment 1, also in this step, a part of the fluorescence β (noise component) emitted from the fluorescence material floating in liquid on metal film 220 passes through polarizer 122 and reaches light detection section 124. As a result, the measurement result (output Os) of this step is mainly composed of a noise component.

It is to be noted that the order of the measurement of the first light (step S140) and the measurement of the second light (step S150) is not limited to the above-mentioned order. For example, the intensity of the first light may be measured after the intensity of the second light is measured.

At step S160, for example, control section 130 counts the number of times of the measurement of the second light (the number of times of s-polarization measurement Cs). When the Cs has not reached a predetermined value (for example, N times), control section 130 again adjusts the rotation angle of polarizer 122 to an angle for detecting the first light, and returns to step S140 to measure the intensity of the first light.

When the Cs has reached N times, control section (processing section) 130 analyzes the output signal (output Op and Os) from light detection section 124 to analyze the presence of the detection object substance or the amount of the detection object substance (step S170).

To be more specific, as illustrated in FIG. 6, control section (processing section) 130 calculates the difference value between output Op and output Os to obtain the signal value for each set of the intensity of the first light measured at step S140 and the intensity of the second light measured at succeeding step S150. Accordingly, when the intensity of the first light and the intensity of the second light are continuously measured, a signal value is calculated for each set of the detection value of the intensity of the first light and the detection value of the intensity of the second light. That is, signal values which change with time are calculated. In addition, by performing step S140 to S160 and step S170 in parallel, signal values which change with time can be calculated in real time.

Figure 8A:
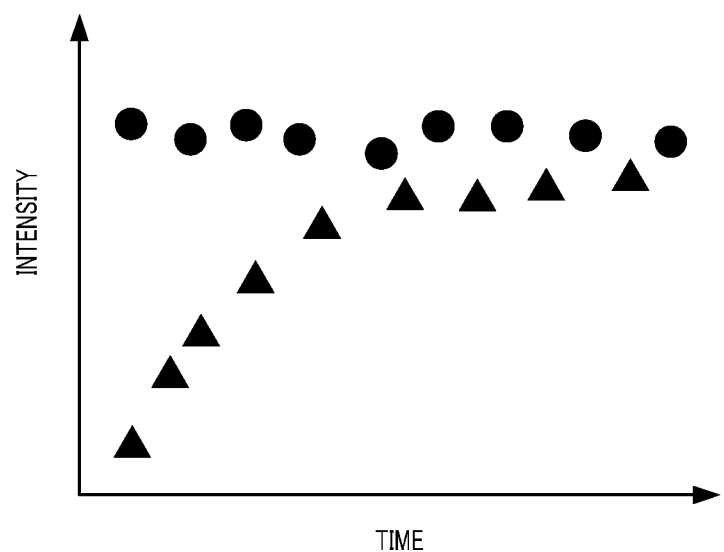
FIGS. 8A and 8B are graphs illustrating example results of measurement of the intensity of the fluorescence in real time.
Figure 8B:
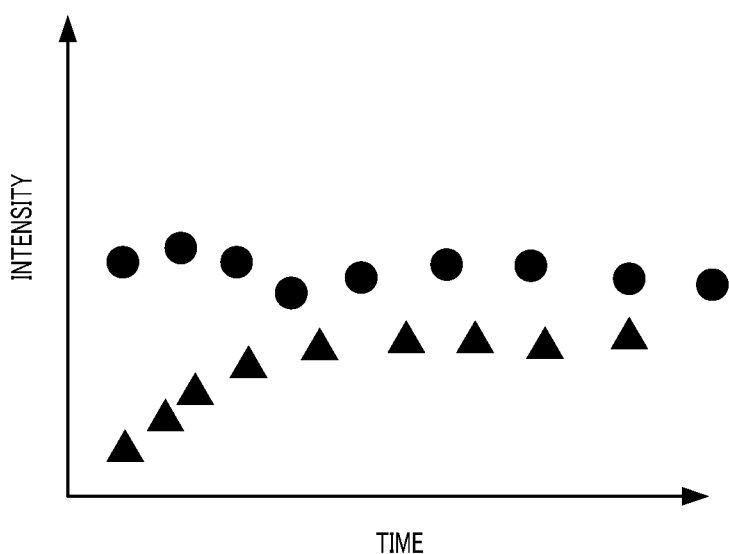

FIG. 8A is a graph illustrating the fluorescence intensity of the signal component and time variation of the fluorescence intensity of the signal component in the case where fluorescence labeling solution containing a fluorescence material at a common concentration (for example, several 100 pM to 1 μM) is provided on metal film 220. FIG. 8B is a graph illustrating the fluorescence intensity of the signal component and time variation of the fluorescence intensity of the signal component in the case where fluorescence labeling solution containing a fluorescence material at a low concentration (for example, 100 fM to several 100 pM) is provided on metal film 220. In these experiments, the intensities of the first light and the second light are measured in the state where the fluorescence labeling solution (free secondary antibody) presents on metal film 220. In the graphs, black circle (•) represents the fluorescence intensity of the noise component (output Os), and black triangle (▲) represents the fluorescence intensity of the signal component (the difference value between output Op and output Os).

From the graphs, it can be said that time variation of the fluorescence intensity of the signal component can be measured regardless of the concentration of the fluorescence material supplied for labelling fluorescence. By kinetic analysis, the measurement values can be indicated in the form of a curve showing the behavior of time variation in a prompt manner.

Through the above-mentioned procedure, the presence of the detection object substance or the amount of the detection object substance in the sample can be measured in real time.

As described above, SPFS device 100' of the present embodiment can detect only the signal component in real time by utilizing the difference between the signal component and the noise component in polarization characteristics, and therefore can measure the detection object substance in real time with high sensitivity comparable to that of conventional SPFS devices.

In addition, SPFS device 100' of the present embodiment can remove the noise component contained in fluorescence β, and therefore can measure the detection object substance without removing the free secondary antibody after the secondary reaction (step S130).

Accordingly, the measurement method according to the present embodiment can detect materials such as lectin which have weak affinity and are difficult to detect with typical sandwich assays. In addition, even in the case where samples such as serum which contain a large number of impurities are used, the intensity of the fluorescence originating from the detection object substance captured on diffraction grating 230 can be discriminated from the intensity of the fluorescence originating from impurities, and consequently it is possible to obtain measurement results in which the influence of noise of the impurities is not substantially reflected while ensuring high accuracy of the measurement.

Accordingly, with the measurement method according to the present embodiment, it is possible to simply measure the detection object substance in unrefined samples such as an original sample collected in a laboratory test, and a crude product of biosynthesis of a new biological substance with high accuracy on a time-series basis.

Figure 9:
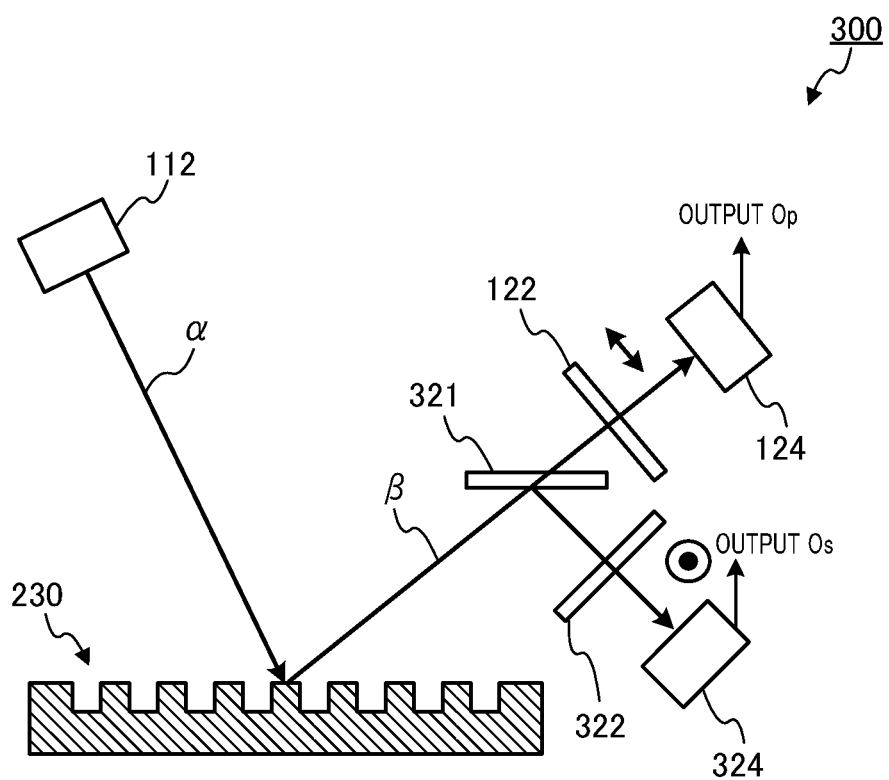
FIG. 9 is a schematic view illustrating another example configuration of the SPFS device according to Embodiments 1 and 2.

It is to be noted that SPFS device 300 illustrated in FIG. 9 may be used in place of SPFS device 100 (100') illustrated in FIG. 1. As illustrated in FIG. 9, the configuration of SPFS device 300 is identical to that of SPFS device 100 except that SPFS device 300 further includes half mirror 321, polarizer 322 and light detection section 324.

Half mirror 321 is disposed on the light path of fluorescence β between diffraction grating 230 and polarizer 122. Light detector 324 is disposed on the light path of fluorescence β reflected by half mirror 321 (reflection light path), and polarizer 322 is disposed on the reflection light path between half mirror 321 and light detector 324. The rotation angle of polarizer 122 is adjusted (or fixed) such that first light (for example, p-polarization light) is allowed to pass therethrough, and the rotation angle of polarizer 322 is adjusted (or fixed) such that second light (for example, s-polarization light) is allowed to pass therethrough. It is to be noted a polarization beam splitter may be used in place of half mirror 321, polarizer 122 and polarizer 322.

Light detectors 124 and 324 successively detect the intensity of the first light and the intensity of the second light, respectively. Accordingly, when excitation light α is successively irradiated by light source 112, light detectors 124 and 324 successively detects the intensity of the first light and the intensity of the second light, respectively. From the viewpoint of preventing excessive discoloration of fluorescence β, when excitation light α is intermittently irradiated by light source 112 at a predetermined interval, light detector 124 intermittently detects the intensity of the first light, and light detector 324 intermittently detects the intensity of the second light. That is, both of the intensity of the first light and the intensity of the second light are simultaneously detected at the interval identical to that of the interval of irradiation of excitation light α.

From output Op from light detector 124 and output Os from light detector 324, graphs similar to FIG. 8A and FIG. 8B can be created.

SPFS device 100 (100') includes only one polarizer 122 and only one light detector 124, and is advantageous in terms of downsizing of the device. Meanwhile, SPFS device 300 can simultaneously measure both of the first light and the second light, and is therefore advantageous in terms of achieving real-time SPFS measurement with higher time resolution.

Reference Experiment

This experiment shows results of examination on polarization characteristics of the fluorescence emitted from a fluorescence material excited on a metal film (a signal component representing the presence or amount of the detection object substance), and the fluorescence emitted from the fluorescence material floating in liquid (a noise component) with use of a measurement device and a measurement method utilizing GC-SPFS.

Figure 10A:
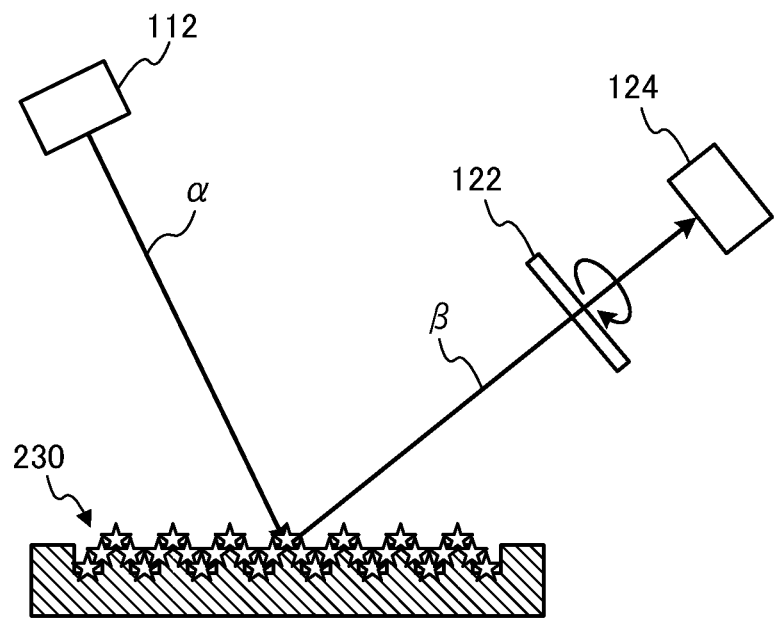
FIGS. 10A and 10B are schematic views illustrating procedure of a reference experiment.

First, as illustrated in FIG. 10A, a first fluorescence material (allophycocyanin, absorption wavelength: 650 nm, fluorescence wavelength 661 nm) indicated by white star marks in the drawing were immobilized on diffraction grating 230 of a metal film. The first fluorescence material simulates a fluorescence material which labels the detection object substance in GC-SPFS. In this state, diffraction grating 230 is irradiated with excitation light α(wavelength 640 nm) at a predetermined incident angle, and the intensity of fluorescence β was measured with light detection section 124 while rotating polarizer (polarization plate) 122. It is to be noted that, in FIG. 10A, buffer solution which is present on diffraction grating 230 is omitted.

Figure 10B:
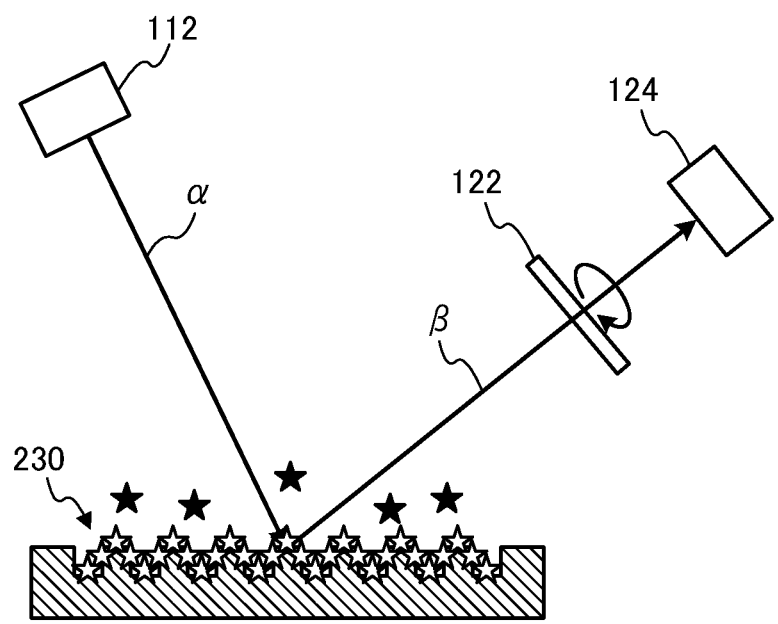

Next, as illustrated in FIG. 10B, on diffraction grating 230 of the metal film, buffer solution containing a second fluorescence material (AlexaFluor 647, absorption wavelength: 647 nm, fluorescence wavelength 665 nm) indicated by black star marks in the drawing was provided. The second fluorescence material simulates a fluorescence material floating in liquid on the metal film which is the noise source in GC-SPFS. In this state, diffraction grating 230 is irradiated with excitation light α (wavelength 640 nm) at the incident angle identical to that of the previous case, and the intensity of fluorescence β was measured with light detection section 124 while rotating polarizer (polarization plate) 122. It is to be noted that, also in FIG. 10B, the buffer solution which is present on diffraction grating 230 is omitted except for the second fluorescence material. Typically, the actual particle size of the fluorescence material is about several nanometers.

Figure 11:
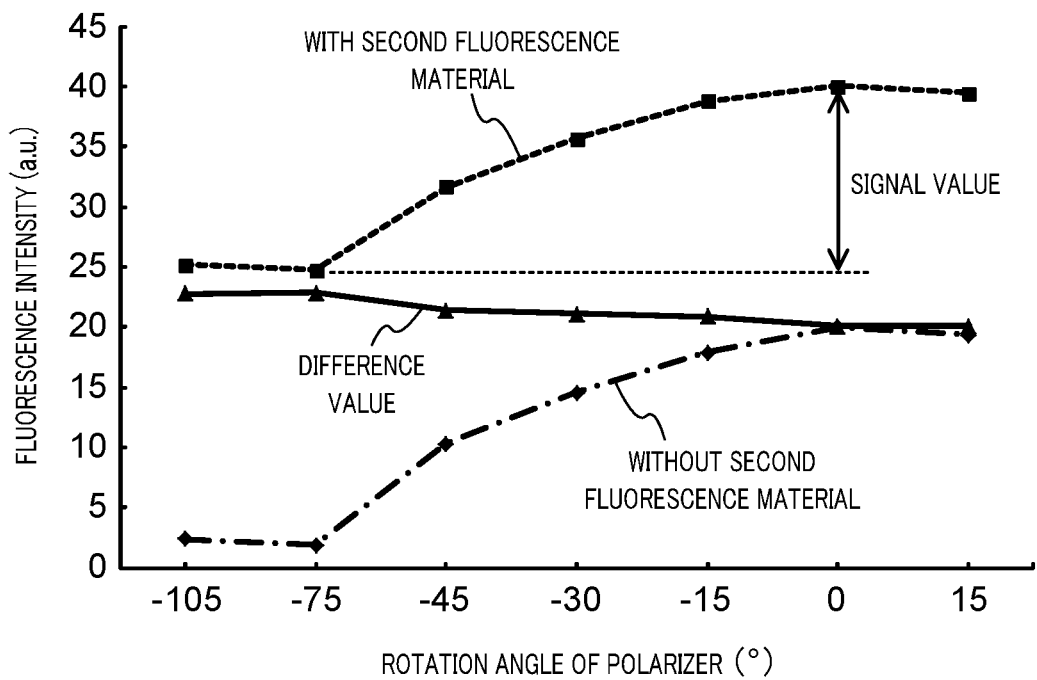
FIG. 11 is a graph illustrating measurement results of the reference experiment.

FIG. 11 is a graph showing a measurement result of the intensity of the fluorescence. The dashed line is a curve representing the relationship between the rotation angle of the polarizer and the intensity of the fluorescence in the case where only the first fluorescence material is present (see FIG. 10A). The broken line is a curve representing the relationship between the rotation angle of the polarizer and the intensity of the fluorescence in the case where the second fluorescence material is present as well as the first fluorescence material (see FIG. 10B). The solid line is a curve representing the relationship of the difference value between the two measurement values and the rotation angle of the polarizer. It is to be noted that the rotation angle of the polarizer is an angle to the plane including the normal to the surface of metal film 220 and the optical axis of excitation light α. For example, p-polarization light is detected when the rotation angle of the polarizer is 0°, and s-polarization light is detected when the rotation angle of the polarizer is ±90°.

First, it is confirmed from the dashed line that the fluorescence originating from the first fluorescence material (signal component) is mainly p-polarization. Next, it is confirmed from the broken line that the intensity of the fluorescence is uniformly raised regardless of the rotation angle of the polarizer when the second fluorescence material floats. One conceivable reason for this is that the fluorescence originating from the second fluorescence material (noise component) is added. In view of this, it is confirmed from the solid line representing the difference value therebetween that the fluorescence originating from the second fluorescence material (noise component) is random polarization.

Accordingly, even when the noise component other than the signal component is contained in the fluorescence, the value of the signal component containing almost no noise component can be calculated by subtracting the detection result of the s-polarization component from the detection result of the p-polarization component, as illustrated in FIG. 11.

INDUSTRIAL APPLICABILITY

The surface plasmon enhanced fluorescence measurement device and the surface plasmon enhanced fluorescence measurement method according to the embodiments of the present invention can measure the detection object substance with high reliability, and is suitable for laboratory test and the like, for example.

In addition, the surface plasmon enhanced fluorescence measurement device and the surface plasmon enhanced fluorescence measurement method according to the embodiments of the present invention can measure the detection object substance with high reliability in real time without washing the surface of the metal film after provision of fluorescence labeling solution and the like. Accordingly, not only reduction in measurement time, but also contribution to development, spread and progression of a very simple quantitative immunity measurement system can be expected.

REFERENCE SIGNS LIST 100, 100', 300 Surface plasmon enhanced fluorescence measurement device (SPFS device)
110 Excitation light irradiation unit
112 Light source
120 Fluorescence detection unit
122, 322 Polarizer
124, 324 Light detection section
130 Control section (processing section)
200 Chip

210 Substrate
220 Metal film
230 Diffraction grating
321 Half mirror
α Excitation light
β Fluorescence
γ Reflection light

The invention claimed is:

1. A surface plasmon enhanced fluorescence measurement device, comprising:
    a chip including a metal film on which a diffraction grating is formed and a capturing body immobilized on the diffraction grating, wherein a detection object substance labeled with a fluorescence material is couplable with the capturing body,
    a light source irradiating the diffraction grating with excitation light to excite the fluorescence material with an enhanced electric field such that the fluorescence material emits fluorescence;
    a polarizer extracting linear polarization light from the fluorescence emitted from the fluorescence material; and
    a light detector detecting the linear polarization light extracted by the polarizer, whereby a presence or an amount of the detection object substance is detectable by the surface plasmon enhanced fluorescence measurement device by irradiating the diffraction grating with the excitation light.

2. The surface plasmon enhanced fluorescence measurement device according to claim 1 further comprising a processing section processor processing a detection value of the light detection section detector, wherein:
    the polarizer simultaneously or separately extracts, from the fluorescence emitted from the fluorescence material, first light in which an angle of a direction of electric field oscillation with respect to a plane including a normal to a surface of the metal film and an optical axis of the excitation light is 0±30° and second light in which an angle of a direction of electric field oscillation with respect to the plane is 90±30°;
    the light detection section detector detects each of the first light and the second light; and
    the processing section processor calculates a difference value between a detection value of the first light and a detection value of the second light.

3. The surface plasmon enhanced fluorescence measurement device according to claim 2, wherein:
    the first light is p-polarization light with respect to the surface of the metal film; and
    the second light is s-polarization light with respect to the surface of the metal film.

4. The surface plasmon enhanced fluorescence measurement device according to claim 1, wherein the excitation light is applied to the metal film at a predetermined incident angle $\theta_1$ and the fluorescence is emitted at an emission angle $\theta_2$ that is different from the incident angle, the incident angle $\theta_1$ and the emission angle $\theta_2$ are each relative to a line normal to the metal film.

5. The surface plasmon enhanced fluorescence measurement device according to claim 1, wherein the excitation light is applied to the metal film at a predetermined incident angle $\theta_1$ at which an intensity of the enhanced electric field formed by surface plasmon resonance is maximized.

* * * * *